United States Patent

Darms et al.

[11] 4,176,124
[45] Nov. 27, 1979

[54] SILICON-MODIFIED PHTHALIC ACID DERIVATIVES

[75] Inventors: Roland Darms, Therwil; Siegfried Wyler, Dornach, both of Switzerland; Gerd Greber, Bad Vüslau, Austria

[73] Assignee: Ciba-Geigy Corporation, Ardsley, N.Y.

[21] Appl. No.: 938,171

[22] Filed: Aug. 30, 1978

[30] Foreign Application Priority Data

Sep. 9, 1977 [CH] Switzerland ............... 11066/77

[51] Int. Cl.² ................. C07F 7/02; C07F 7/04; C07F 7/18
[52] U.S. Cl. ............... 260/346.3; 260/448.8 R; 560/19; 560/48
[58] Field of Search ............ 260/346.3, 448.8 R

[56] References Cited

U.S. PATENT DOCUMENTS 3,853,935  12/1974  Roshdy et al. ............ 260/448.8 R
4,005,117  1/1977   Heckert et al. ........... 260/448.8 R

OTHER PUBLICATIONS

Hopff et al., Chemical Abstracts, vol. 68 (1968) 106060p.

Primary Examiner—Richard Raymond
Attorney, Agent, or Firm—Joseph F. DiPrima

[57] ABSTRACT

The invention relates to Si-modified phthalic acid derivatives (acids, esters and anhydrides) of the formula I

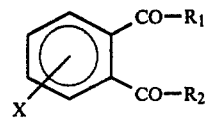

in which $R_1$ and $R_2$ independently of one another are —OH, alkoxy with 1-12 C atoms or phenoxy or $R_1$ and $R_2$ together are the —O— group, X is a

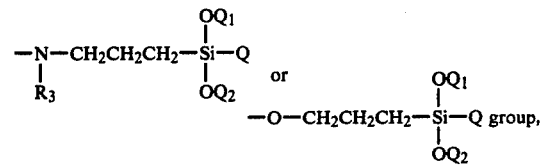

$R_3$ is alkyl with 2-7 C atoms, cycloalkyl with 5-7 C atoms, benzyl or

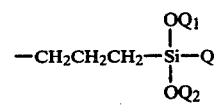

Q is methyl, phenyl or —$OQ_3$ and $Q_1$, $Q_2$ and $Q_3$ independently of one another are alkyl with 1-6 C atoms or phenyl.

The products of the invention are prepared by reacting the corresponding allylamino-phthalic anhydrides or allylamino-phthalic acid esters with compounds of the formula III

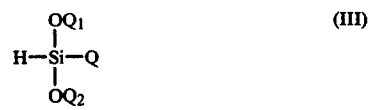

They are used as adhesion promoters, for example between inorganic solids and organic resins. They may also be used for the preparation of other Si-modified adhesion promoters, and as curing agents for epoxide resins.

4 Claims, No Drawings

SILICON-MODIFIED PHTHALIC ACID DERIVATIVES

The present invention relates to novel silicon-modified phthalic acid derivatives, to a process for their preparation, and to their use as adhesion promoters, for example between inorganic solids and organic resins. The novel phthalic acid derivatives can also be used to prepare other silicon-modified adhesion promoters, and/or as curing agents for epoxide resins.

The literature discloses that various silanes, for example vinyltrichlorosilane, vinyl-tris-(2-methoxy)silane and γ-aminopropyltriethoxysilane, may be used as adhesion promoters for various applications, for example for the production of glass fibre-reinforced plastics, for sealants, for lacquers and for adhesives [compare, for example, Defazet, 28, 207–211 (1974) and Kunststoffe, 55, 909–912 (1965)]. However, the properties of the products obtained using these known adhesion promoters in part leave something to be desired, especially in respect of water absorption, resistance to thermal oxidation and/or electrical properties.

It is the object of the present invention to provide novel adhesion promoters or novel intermediates for the preparation of adhesion promoters, by means of which the above disadvantages may be avoided.

The novel silicon-modified phthalic acid derivatives correspond to the formula I

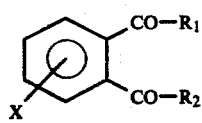

in which $R_1$ and $R_2$ independently of one another are —OH, alkoxy with 1–12 C atoms or phenoxy or $R_1$ and $R_2$ together are the —O— group, X is a

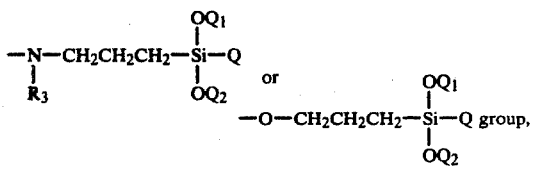

$R_3$ is alkyl with 2–7 C atoms, cycloalkyl with 5–7 C atoms, benzyl or

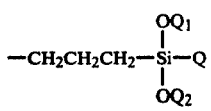

Q is methyl, phenyl or —$OQ_3$ and $Q_1$, $Q_2$ and $Q_3$ independently of one another are alkyl with 1–6 C atoms or phenyl.

The compounds of the formula I may be prepared by a method wherein a compound of the formula II

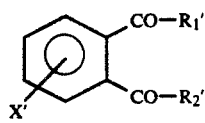

in which $R_1'$ and $R_2'$ independently of one another are alkoxy with 1–12 C atoms or phenoxy or $R_1'$ and $R_2'$ together are —O—, X' is a

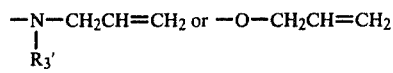

group and $R_3'$ is alkyl with 2–7 C atoms, cycloalkyl with 5–7 C atoms, benzyl or allyl, is reacted with at least the stoichiometric amount of a compound of the formula III

in which Q, $Q_1$ and $Q_2$ are as defined under formula I, after which the resulting compound in which $R_1'$ and $R_2'$ together are —O— may or may not be converted to the corresponding free acid.

Alkoxy groups $R_1$ and/or $R_2$ and alkyl groups $R_3$, $R_3'$, $Q_1$, $Q_2$ and $Q_3$ may be straight-chain or branched. As examples of alkoxy or alkyl groups according to the definition there may be mentioned the methoxy, ethoxy, n-propoxy, isopropoxy, n-hexyloxy, n-decyloxy and n-dodecyloxy group and the methyl, ethyl, n-propyl, isopropyl, n-butyl, tert.-butyl, n-pentyl, n-hexyl and n-heptyl group.

$R_1$ and $R_2$ are preferably —OH or alkoxy with 1–4 C atoms, especially methoxy or ethoxy. Compounds where $R_1$ and $R_2$ together are the —O— group are, however, very particularly preferred.

Where $R_3$ or $R_3'$ is an alkyl group, it is especially an alkyl group with 2–4 C atoms and more particularly the ethyl or isopropyl group.

Where $R_3$ or $R_3'$ is a cycloalkyl group, it is, for example, the cyclopentyl group and especially the cyclohexyl group.

Alkyl groups $Q_1$, $Q_2$ and/or $Q_3$ preferably have a straight chain and contain 1–6, and especially 1–4, C atoms.

The grouping X is preferably bonded to the benzene ring in the 3-position.

Preferred compounds of the formula I are those in which $R_1$ and $R_2$ together are the —O— group, X is a

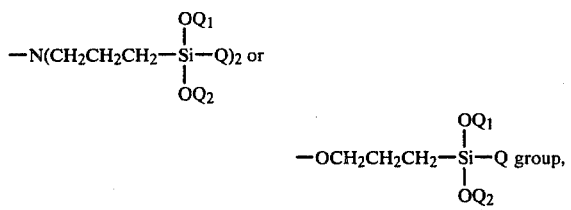

bonded in the 3-position, Q is methyl or alkoxy with 1–4 C atoms and $Q_1$ and $Q_2$ are each alkyl with 1–4 C atoms.

The starting compounds of the formula III are known.

Starting compounds of the formula II, in which X' is a diallylamino group, may be obtained by reacting an aminophthalic acid derivative of the formula IV

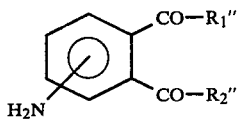 (IV)

in which $R_1''$ and $R_2''$ independently of one another are —OH or a —O⁻M⁺ group, or $R_1''$ and $R_2''$ together are $(—O^-)_2 M_1^{++}$, M⁺ is an alkali metal cation, a trialkylammonium cation with 3–24 C atoms or a quaternary ammonium cation and $M_1^{++}$ is an alkaline earth metal cation, with an allyl halide, especially allyl bromide or allyl chloride, and then converting the resulting N,N-bis-allylaminophthalic acid into a derivative of the formula II, for example by cyclising to the anhydride or esterifying with corresponding alcohols.

Starting compounds of the formula II, in which X' is a —OCH₂CH=CH₂ group, may be prepared by reacting a compound of the formula V

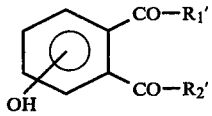 (V)

in which $R_1'$ and $R_2'$ are as defined under formula II, with an allyl halide, preferably allyl bromide or allyl chloride, in the presence of a base, for example an alkali metal carbonate, for example potassium carbonate.

Starting compounds of the formula II, in which X' is a

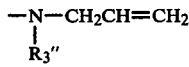

group and $R_3''$ is alkyl with 2–7 C atoms, cycloalkyl with 5–7 C atoms or benzyl, are novel compounds and are also a subject of the present invention. They may be obtained by reacting a compound of the formula VI

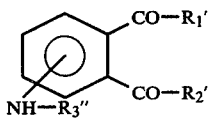 (VI)

in which $R_1'$, $R_2'$ and $R_3''$ have the above meaning, with an allyl halide, especially allyl bromide or allyl chloride, preferably in the presence of a base, for example an alkali metal carbonate or alkali metal hydroxide, for example potassium carbonate, potassium hydroxide or sodium hydroxide.

The above reactions with allyl halides are advantageously carried out in a polar medium, especially in an aqueous medium, at temperatures between about 0° C. and 100° C., especially between about 25° and 80° C.

The compounds of the formulae V and VI are known or may be prepared by methods known per se.

The reaction of the compounds of the formula II with the silanes of the formula III is advantageously carried out in an anhydrous organic medium and in the presence of a catalyst. Examples of catalysts which may be used are organic peroxides, such as tert.-butyl hydroperoxide, di-tert.-butyl peroxide, peracetic acid, benzoyl peroxide, diacyl peroxides and cumene hydroperoxide, or platinum or palladium catalysts, for instance platinum/charcoal catalysts or $PtCl_6H_2$ catalysts.

Examples of suitable inert organic solvents are aromatic hydrocarbons, for instance benzene, toluene and xylenes, cyclic ethers, for instance tetrahydrofuran, tetrahydropyran and dioxane, and ethylene glycol monoalkyl ethers and dialkyl ethers each with 1–4 C atoms in the alkyl portions, for instance ethylene glycol monomethyl ether, monoethyl ether, diethyl ether and di-n-butyl ether.

Aromatic hydrocarbons are preferred solvents.

The reaction is advantageously carried out under a protective gas, for example nitrogen or argon.

The reaction temperatures are in general approximately between 80° and 150° C.; reaction temperatures between about 90° and 120° C. are preferred.

The compounds of the formulae II and III are employed in approximately stoichiometric amount. Preferably a slight excess of silane of the formula III is employed, for example an excess of about 10–50%.

The optional hydrolysis of the resulting anhydrides to the free acids can be carried out in accordance with conventional methods.

After completion of the reaction, the solvent and any excess silylating agent present are removed in the conventional manner, for example by distilling off in vacuo.

The compounds of the formula I are in general obtained in the form of pale yellow to reddish oils.

As mentioned at the outset, the compounds of the formula I are also valuable intermediates for the preparation of other silicon-modified adhesion promoters, for example compounds of the formula VII

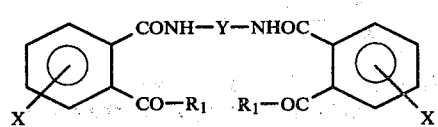 (VII)

as well as the corresponding cyclised imide derivatives. In the formula VII X and $R_1$ are as defined under formula I and Y is a structural element of the formula VIII

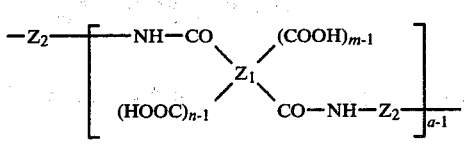 (VIII)

in which a is an integer from 1 to 15, especially 1 to 10, m and n independently of one another are 1 or 2, $Z_1$ is an aliphatic radical with at least two carbon atoms, or a cycloaliphatic, carbocyclic-aromatic or heterocyclic-aromatic radical in which the carboxamide groups and carboxyl groups are bonded to different C atoms and carboxyl groups bonded to $Z_1$ are each in the ortho-position to a carboxamide group, and the individual radicals $Z_2$ independently of one another are an aliphatic radical with at least two C atoms or a cycloaliphatic, araliphatic, carboxylic-aromatic or heterocyclic-aromatic radical.

Preferably, $Z_1$ and $Z_2$ are carbocyclic-aromatic radicals. In particular, if m and n are 1, $Z_1$ is the 1,3- or 1,4-phenylene group, if m is 1 and n is 2, $Z_1$ is a benzenetriyl group, and if m and n are 2, $Z_1$ is a benzenetetrayl group or the benzophenone ring system. Preferred meanings of $Z_2$ are the 1,3- or 1,4-phenylene group, the 4,4'-diphenylmethane radical, the 4,4'-diphenyl-ether radical or the 4,4'-diphenylsulphone radical.

The compounds of the formula VII may be prepared in a manner known per se, by reacting at least stoichiometric amounts of a compound of the formula I or of a mixture of two different compounds of the formula I with diamines $H_2N-Y-NH_2$. The reaction is advantageously carried out in an inert organic solvent or in a solvent mixture, examples of suitable solvents being N,N-dialkylamides of aliphatic monocarboxylic acids with 1-3 C atoms in the acid part, for example N,N-dimethylformamide or N,N-dimethylacetamide, cyclic amides, for example N-methyl-2-pyrrolidone, cyclic ethers or ethylene glycol monoalkyl ethers or dialkyl ethers with 1-4 C atoms in each alkyl part, for example tetrahydrofuran, dioxane and ethylene glycol monomethyl ether, monoethyl ether, diethyl ether and di-n-butyl ether.

The compounds of the formula I and especially the derivatives of the formula VII which may be prepared therefrom are valuable adhesion promoters, especially between inorganic solids and organic resins, and may be used for a large number of applications in the adhesives industry and in the lacquer-using and plastics-processing industries.

The following are examples of some fields of use: improving the adhesion of special sealants, for example polysulphides, polyurethanes and polyacrylates, to various substrates, for example glass, aluminium and ceramics; encapsulating mineral fillers so as to improve the mechanical properties of the products obtained therewith, for example in the case of sand-filled masks and cores used in the foundry industry, mineral-filled cable mixtures or other mineral-filled plastics, for example filled thermosetting resins, for instance quartz-filled epoxide resins and filled unsaturated polyesters, filled thermoplastics, for instance polyamide-6,6 and polyethylene terephthalate, and filled elastomers, for instance natural rubber and synthetic rubber; and incorporation in adhesives, adhesive compositions and lacquers, for example adhesive compositions containing epoxide resins, and lacquers based on epoxides, polyacrylates, polyurethanes and vinyl chloride copolymers. However, the compounds mentioned are especially suitable for the manufacture of reinforced plastics, especially glass fibre-reinforced plastics, in particular composite materials, for instance laminates, in order to improve the adhesion between the substrate or matrix and the plastic applied thereto. The substrate per se may be in any desired form, for example in the form of fibres, fabrics or nonwovens, and preferably consists of glass or of mineral materials, for example quartz, mineral wool, asbestos, mica or metal fibres and foils. Examples of suitable plastics for the manufacture of such laminates are acrylates and polyester, epoxide, silicon, melamine, phenolic and furan resins, and also polyamides, polyamidoacids and polyimides, but especially polymers crosslinkable via C=C double bonds, for instance unsaturated polyesters, homopolymers and copolymers containing maleimidyl or nadicimidyl groups, their precursors or their mixtures with other polymers.

Relative to comparable composite materials which have been manufactured using known silicon-containing adhesion promoters, especially those of the type mentioned at the outset, glass fibre-reinforced composite materials manufactured using the adhesion promoters according to the invention, of the formula I, or the abovementioned derivatives thereof, are distinguished especially by improved resistance to thermal oxidation, improved dielectric properties after exposure to moisture, and/or lower water absorption. The compounds of the formula I and the derivatives prepared therefrom are also distinguished by good wetting of the substrates.

The adhesion promoters according to the invention, and derivatives thereof, are advantageously applied in the form of solutions in suitable organic solvents, for example N,N-dimethylformamide, N,N-dimethylacetamide, N-methyl-2-pyrrolidone, acetone, methyl ethyl ketone, tetrahydrofuran and dioxane, or in the form of aqueous dispersions or emulsions, in accordance with conventional techniques.

Compounds of the formula I, in which $R_1$ and $R_2$ together are —O—, may also be used as curing agents for epoxide resins. Corresponding curable mixtures, which may be used for the production of mouldings, impregnations, coatings, glue bonds and the like, contain a polyepoxide compound and, as the curing agent, one or more compounds of the formula I, in which $R_1$ and $R_2$ together are —O—, with or without further additives.

Suitable polyepoxide compounds are all those which can be cured with anhydride curing agents. Specific examples are:

Alicyclic polyepoxides, for instance epoxyethyl-3,4-epoxycyclohexane (vinylcyclohexane diepoxide), limonene diepoxide, dicyclopentadiene diepoxide, bis-(3,4-epoxycyclohexylmethyl) adipate, (3',4'-epoxycyclohexylmethyl)-3,4-epoxycyclohexanecarboxylate, (3',4'-epoxy-6'-methylcyclohexylmethyl)-3,4-epoxy-6-methylcyclohexanecarboxylate, 3-(3',4'-epoxycyclohexyl)-2,4-dioxaspiro-(5,5)-8,9-epoxyundecane and 3-(glycidyloxyethoxyethyl)-2,4-dioxaspiro(5,5)-8,9-epoxyundecane.

Diglycidyl ethers or polyglycidyl ethers of polyhydric alcohols, for example 1,4-butanediol or of polyalkylene glycols, for example polypropylene glycols, diglycidyl ethers or polyglycidyl ethers of cycloaliphatic polyols, for example 2,2-bis-(4-hydroxycyclohexyl)-propane; diglycidyl ethers or polyglycidyl ethers of polyhydric phenols, for example resorcinol, bis-(p-hydroxyphenyl)methane, 2,2-bis-(p-hydroxyphenyl)-propane (diomethane), 2,2-bis-(4'-hydroxy-3',4'-dibromophenyl)-propane and 1,1,2,2-tetrakis-(p-hydroxyphenyl)-ethane, or of condensation products of phenols with formaldehyde, obtained under acid conditions, for example phenol novolacs and cresol novolacs; and di- or poly-($\beta$-methylglycidyl) ethers of the abovementioned polyalcohols and polyphenols.

Polyglycidyl esters and poly-($\beta$-methylglycidyl) esters of polybasic carboxylic acids, for example phthalic acid, terephthalic acid, tetrahydrophthalic acid and hexahydrophthalic acid.

N-Glycidyl derivatives of amines, amides and heterocyclic nitrogen bases, for example N,N-diglycidylaniline, N,N-diglycidyltoluidine, N,N,N',N'-tetraglycidyl-bis-(p-aminophenyl)-methane, triglycidyl isocyanurate, N,N'-diglycidylethyleneurea, N,N'-diglycidyl-5,5-dimethylhydantoin, N,N'-diglycidyl-5-isopropylhydantoin and N,N'-diglycidyl-5,5-dimethyl-6-isopropyl-5,6-dihydrouracil.

Active diluents may or may not be added to the curable mixtures to lower the viscosity, examples of such diluents being styrene oxide, butyl glycidyl ether, isooctyl glycidyl ether, phenyl glycidyl ether, cresyl glycidyl ether, and glycidyl esters of synthetic, highly branched, mainly tertiary aliphatic monocarboxylic acids.

In addition, curing accelerators may be employed for the curing reaction. Examples of such accelerators are tertiary amines, their salts or quaternary ammonium compounds, for example 2,4,6-tris-(dimethylaminomethyl)-phenol, benzyldimethylamine, 1-methylimidazole, 2-ethyl-4-methyl-imidazole, 4-aminopyridine and triamylammonium phenolate, or alkali metal alcoholates, for example sodium hexanetriolate. The curing is advantageously carried out in the temperature range of 50° C. to 250°, preferably of 120°–220° C.

The curing can, in the known manner, also be carried out in two or more stages, the first being carried out at a low temperature and the post-curing at a higher temperature.

Curing may, if desired, also be carried out in 2 stages by first prematurely stopping the curing reaction or carrying out the first stage at only slightly elevated temperature, whereby a curable precondensate which is still fusible and/or soluble (a so-called "B-stage") is obtained from the epoxide component (a) and the curing agent (b). Such a precondensate can be used, for example, for the manufacture of "prepegs", compression moulding compositions or, in particular, sintering powders.

The term "curing" as used here means converting the soluble, either liquid or fusible, polyepoxides into solid, insoluble and infusible, three-dimensionally crosslinked products or materials, as a rule with simultaneous shaping to give shaped articles, for example castings, compression mouldings and laminates, impregnations, coatings, lacquer films or glue bonds.

At any stage before curing, there may be added to the curable mixtures extenders, fillers and reinforcing agents, for example coal tar, bitumen, textile fibres, glass fibres, asbestos fibres, boron fibres, carbon fibres, mineral silicates, mica, quartz powder, titanium dioxide, hydrated aluminium oxide, bentonites, kaolin or silica aerogel, or metal powders, for example aluminium powder or iron powder, or pigments and dyes, such as carbon black, oxide colorants, titanium oxide and others. Other conventional additives, for example flameproofing agents, for instance antimony trioxide, thixotropic agents and flow control agents, for instance silicones, waxes or stearates (some of which are also used as mould release agents) may also be introduced into the curable mixtures.

The curable mixtures may be prepared in the conventional manner by means of known mixing equipment (stirrers, kneaders, mills and the like).

The curable epoxide resin mixtures described are employed especially in the fields of surface protection, the electrical industry, laminating processes and the building trade. They may be used, as formulations suited in each case to the particular application, in the filled or unfilled state, as paints, lacquers, compression moulding compositions, dipping resins, casting resins, injection moulding formulations, impregnating resins, adhesives, tooling resins, laminating resins, sealants, putties, floor covering compositions and binders for mineral aggregates.

The following epoxide resin was used for the preparation of the curable mixtures described in the use examples.

Epoxide Resin A

An epoxide resin (technical-grade product) which is produced by condensation of 2,2-bis-(p-hydroxyphenyl)propane with a stoichiometric excess of epichlorohydrin in the presence of alkali, consists in the main of the monomeric diglycidyl ether of the formula

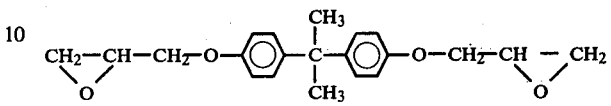

is liquid at room temperature, has an epoxide content of 5.12–5.54 epoxide equivalents/kg and has a viscosity (by the Hoeppler method) of 9,000–13,000 cP at 25° C.

To determine the mechanical properties of the curable mixtures described in the examples which follow, sheets 4 mm thick were prepared. The test specimens for determining the flexural strength, modulus of elasticity and deflection according to VSM Standard Specification 77,103 and the water absorption, measured on flexural test specimens at 23° C., according to VSM Standard Specification 77,103, were machined from the sheets.

PREPARATION EXAMPLES

EXAMPLE 1

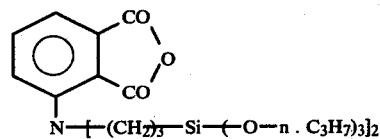

In a sulphonation flask, 50 g (0.205 mol) of 3-N,N-diallylamino-phthalic anhydride are dissolved in 250 ml of anhydrous toluene, under nitrogen, and the solution is heated to 115° C. At this temperature, a solution of 115 g (0.55 mol) of tri-n-propoxysilane and 2 ml of an 0.02 molar hexachloroplatinic acid ($H_2PtCl_6 \cdot 6H_2O$) solution in propanol, in 50 ml of anhydrous toluene, is added dropwise in the course of 20 minutes, with stirring. The reaction mixture is then stirred for a further 10 hours at 110° C. The solvent and the excess tri-n-propoxysilane are removed in vacuo. 111 g (83% of theory) of 3-N,N-bis-[3-(tri-n-propoxy)-silyl-propyl]-aminophthalic anhydride are obtained in the form of a reddish oil.

Analysis for $C_{32}H_{47}NO_9Si_2$ (molecular weight 656): Calculated: C 58.59% H 8.76% N 2.14% Si 8.56%; Found: C 59.0% H 8.4% N 2.5% Si 8.0%.

3-N,N-Diallylamino-phthalic anhydride, used as a starting material, may be prepared as follows: 225 g (1.0 mol) of disodium 3-aminophthalate and 138 g (1.0 mol) of potassium carbonate are dissolved in 400 ml of water. 317.2 g (2.6 mols) of allyl bromide are added to the solution at about 25° C. and the reaction mixture is stirred for 4 hours at 30°–35° C. The diallylaminophthalic acid is precipitated by adding 200 ml of 35% hydrochloric acid. The product is filtered off at 10° C., washed with 100 ml of water and dried. 261 g (1 mol) of the resulting 3-N,N-diallylaminophthalic acid are heated to 150°–155° C. A melt is formed, which is stirred for 2 hours at about 150° C. whilst passing a stream of nitrogen over the material, and is then allowed to cool to 50° C. 750 ml of toluene and 750 ml of n-hexane are then added and the crude product is crystallised from this mixture. 237 g of 3-N,N-diallylaminophthalic anhydride, of melting point 94°–95° C., are obtained.

EXAMPLE 2

Following the procedure described in Example 1, 50 g (0.205 mol) of 3-N,N-diallylaminophthalic anhydride in 250 ml of anhydrous toluene are reacted with 136.5 g (0.41 mol) of tri-n-hexyloxysilane and 2 ml of 0.02 molar hexchloroplatinic acid in 50 ml of toluene. After removing the solvent and the excess silylating agent, 186 g (100% of theory) of 3-N,N-bis-[3-(tri-n-hexyloxy)-silyl-propyl]-aminophthalic anhydride are obtained in the form of a reddish oil.

Analysis for $C_{50}H_{93}NO_9Si_2$ (molecular weight 908): Calculated: C 66.11% H 10.32% N 1.54% Si 6.18%; Found: C 66.1% H 10.5% N 1.7% Si 6.2%

EXAMPLE 3

In a sulphonation flask, 18.7 g (0.08 mol) of 3-N-ethyl-N-allylaminophthalic anhydride are dissolved in 300 ml of anhydrous toluene, under nitrogen, and the solution is heated to 105° C. At this temperature 25.6 g (0.124 mol) of tri-n-propoxysilane and 0.6 ml of an 0.02 molar solution of hexachloroplatinic acid in propanol are added dropwise in the course of 45 minutes, with stirring. The mixture is then stirred for a further 3 hours at 110° C. After evaporating off the solvent, the residue is distilled in a high vacuum. 24.5 g (70% of theory) of 3-N-ethyl-N-(tri-n-propoxy)-silyl-propylaminophthalic anhydride are obtained in the form of a pale yellow oil, boiling point 190°–215° C./$10^{-3}$ mm Hg.

Analysis for $C_{22}H_{35}NO_6Si$ (molecular weight 438): Calculated: C 60.38% H 8.06% N 3.20% Si 6.42%; Found: C 60.6% H 8.1% N 3.4% Si 6.4%.

3-N-Ethyl-N-allylaminophthalic anhydride, used as a starting material, may be prepared as follows:

211.1 g (1 mol) of 3-nitrophthalic acid are dissolved in 1,200 ml of dioxane and hydrogenated at 20°–25° C., using 10 g of a palladium/charcoal catalyst (5% by weight of palladium). 89 g (2 mols) of freshly distilled acetaldehyde in 300 ml of dioxane are then added and the hydrogenation is continued. The catalyst is then removed and the reaction solution is evaporated in vacuo. The residue is repeatedly extracted with hot toluene and the solutions are filtered and then cooled until they crystallise. 82.4 g (43% of theory) of 3-N-ethylaminophthalic anhydride, melting point 133°–134° C., are obtained.

Analysis for $C_{10}H_9NO_3$: Calculated: C 62.82% H 4.75% N 7.33%; Found: C 62.8% H 4.8% N 7.4%.

19.1 g (0.1 mol) of 3-N-ethylaminophthalic anhydride and 13.8 g (0.1 mol) of potassium carbonate are dissolved in 150 ml of water whilst heating to 100° C., with stirring. After the solution has cooled, 13.3 g (0.11 mol) of allyl bromide are added dropwise, whereupon the mixture is again heated to 100° C., in the course of 3 hours. It is then cooled to 20°–25° C., a further 3.5 g of potassium carbonate are added, the mixture is again heated to 100° C. and a further 3.5 g of allyl bromide are added dropwise. After stirring for 1 hour, the solution is cooled (its pH is 7–8) and is acidified to pH 3–4 with concentrated hydrochloric acid. It is then evaporated to dryness and the residue is heated to 160° C. in the course of 1 hour. The crude product is repeatedly extracted with hot cyclohexane. After removing the solvent, 12 g (52% of theory) of 3-N-ethyl-N-allylaminophthalic anhydride, melting point 80°–83° C., are obtained.

Analysis for $C_{13}H_{14}NO_3$: Calculated: C 67.23% H 6.08% N 6.03%; Found: C 67.35% H 6.02% N 5.94%.

EXAMPLE 4

20.4 g (0.1 mol) of 3-allyloxyphthalic anhydride in 250 ml of absolute toluene and 2 ml of a 0.02 molar solution of $H_2PtCl_6.6H_2O$ in n-propanol are first introduced into a 750 ml sulphonation flask, equipped with a stirrer, thermometer, reflux condenser and dropping funnel, whilst excluding moisture. A solution of 23 g (0.11 mol) of tri-n-propoxysilane in 50 ml of absolute toluene and 2 ml of an 0.02 molar solution of $H_2PtCl_6.6H_2O$ in n-propanol are added dropwise in the course of 30 minutes at 110° C. internal temperature, with stirring. After stirring the reaction mixture for 10 hours at 110° C., the solvent is distilled off in vacuo and the oily brown residue obtained is subjected to a Vigreux molecular-path distillation, and fractionated. 3-(γ-Tri-n-propoxysilyl)-propoxyphthalic anhydride is obtained at 160°–165° C./$10^{-3}$ mm Hg.

EXAMPLE 5

In a sulphonation flask, 4.00 g (0.02 mol) of 4,4'-diaminodiphenyl ether are dissolved in 90 ml of anhydrous N,N-dimethylacetamide (DMA), under a nitrogen atmosphere and 3.27 g (0.015 mol) of pyromellitic dianhydride are added in portions at 0° C. The reaction mixture is stirred for one hour at 20°–25° C. 6.56 g (0.01 mol) of the 3-N,N-bis-[3-(tri-n-propoxy)-silyl-propyl]-aminophthalic anhydride prepared according to Example 1 are then added at 0° C. and the reaction mixture is stirred for a further hour at 20°–25° C. The polyamidoacid solution obtained can be used as an adhesion promoter for finishing glass fibre fabrics which can be used for the production of glass fibre-reinforced laminates.

EXAMPLE 6

In a sulphonation flask, 3.24 g (0.03 mol) of m-phenylenediamine are dissolved in 110 ml of DMA, under a nitrogen atmosphere, and the solution is cooled to between −15° C. and −20° C. 5.07 g (0.025 mol) of isophthalic acid dichloride are added dropwise to this solution, with stirring, under conditions such that the temperature does not rise above −15° C. The reaction mixture is then stirred for one hour at 20°–25° C. A solution of 5.06 g (0.05 mol) of triethylamine in 10 ml of DMA is then added dropwise at −15° C. After stirring for a further hour at 20°–25° C., the reaction solution is cooled to 0° C., 9.08 g (0.01 mol) of 3-N,N-bis-[3-(tri-n-hexyloxy)-silylpropyl]-aminophthalic anhydride are added, and the solution is stirred for a further hour at 20°–25° C. After filtering off the triethylamine hydrochloride which has precipitated, the 10% strength polyamide acid solution obtained is used for finishing glass fibre fabrics.

EXAMPLE 7

Using the procedure described in Example 6, 4.96 g (0.025 mol) of 4,4'-diaminodiphenylmethane, 4.0 g (0.02 mol) of trimellitic anhydride chloride, 2.02 g (0.02 mol) of triethylamine and 6.56 g (0.01 mol) of 3-N,N-bis-[3-tri-n-propoxy)-silylpropyl]-aminophthalic anhydride are reacted in 150 ml of anhydrous DMA. The resulting 10% strength polyamide-amidoacid solution can be used for finishing glass fibre fabrics.

EXAMPLE 8

Using the procedure described in Example 1, 50 g (0.205 mol) of 4-N,N-diallylaminophthalic anhydride in 250 ml of anhydrous toluene are reacted with 115 g (0.55 mol) of tri-n-propoxysilane and 2 ml of 0.02 molar hexachloroplatinic acid in 50 ml of toluene. After removing the solvent and the excess silylating agent, 115 g (85% of theory) of 4-N,N'-bis-[3-(tri-n-propoxy)-silyl-propyl]-aminophthalic anhydride are obtained in the form of a reddish oil.

Analysis for $C_{32}H_{57}NO_9Si_2$ (molecular weight: 655.98): Calculated: C 58.59% H 8.76% N 2.14% Si 8.56%; Found: C 58.3% H 8.9% N 2.2% Si 8.9%.

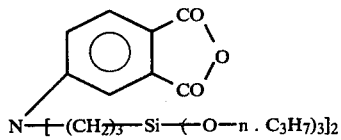

EXAMPLE 9

In a sulphonation flask, 27.2 g (0.105 mol) of 4-(N-butyl-N'-allyl)-aminophthalic anhydride are dissolved in 150 ml of anhydrous toluene, under a nitrogen atmosphere, and the solution is heated to 115° C. At this temperature, a solution of 26 g (0.16 mol) of methyl-di-n-propoxysilane and 1 ml of 0.01 molar hexachloroplatinic acid in 25 ml of toluene is added dropwise in the course of 15 minutes, with stirring. The reaction mixture is then stirred for a further 4 hours, at 110° C. The solvent and excess methyl-di-n-propoxysilane are removed in vacuo. 40 g (90% of theory) of 4-[N-butyl-N'-(methyl-di-n-propoxy)-silyl-propyl]-aminophthalic anhydride are obtained.

Analysis for $C_{22}H_{35}NO_5Si$ (molecular weight 421.66): Calculated: C 62.68% H 8.37% N 3.32%; Found: C 62.4% H 8.6% N 2.9%.

4-(N-Butyl-N'-allyl)-aminophthalic anhydride, used as the starting material, may be prepared as follows: 106 g (6.5 mols) of 4-nitrophthalic acid are dissolved in 1,000 ml of dioxane and hydrogenated at 20°–25° C., using 10 g of a palladium/charcoal catalyst (5% by weight of palladium). 68 ml (55 g=0.75 mol) of butyraldehyde are then added and the hydrogenation is continued. The catalyst is then removed and the reaction solution is evaporated in vacuo. 29.6 g (0.125 mol) of the residue (crude 4-N-butyl-aminophthalic acid) and 17.5 g (0.125 mol) of K carbonate are dissolved in 125 ml of $H_2O$. 18.1 g (0.15 mol) of allyl bromide are added to the solution at 20° to 25° C. and the reaction mixture is stirred for 20 hours at 10° C. and then for 4 hours at 80° C. The 4-(N-butyl-N'-allyl)-aminophthalic acid is precipitated as a dark yellow oil by adding 35% hydrochloric acid. The crude product is taken up in ethyl acetate, the solution is washed with water and dried, and the acid is then cyclised thermally or chemically to 4-(N-butyl-N'-allyl)-aminophthalic anhydride. 17 g (52% of theory) of a dark yellow oil are obtained.

The chemical cyclisation is carried out as described below: 38 ml (0.4 mol) of acetic anhydride are added to 0.25 mol of the above acid and the mixture is stirred for 1 hour at 80°–90° C. The excess acetic anhydride is then distilled off in vacuo. The oily residue is taken up in a solvent mixture of diethyl ether and hexane, 30 g of silica gel are added and the mixture is filtered. After stripping off the solvent, an oily product is obtained. Crude yield: 35 g (80%). The material is then fractionated by molecular path distillation, with addition of Cu powder. 4-(N-Butyl-N'-allyl)-phthalic anhydride is obtained in 50% yield as an oily product of boiling point 185°–190° C./$10^{-2}$ mm Hg.

EXAMPLE 10

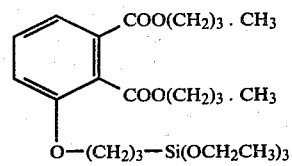

In a sulphonation flask, 16.72 g (0.05 mol) of butyl 3-allyloxy-phthalate are dissolved in 100 ml of anhydrous toluene, under a nitrogen atmosphere, and the solution is heated to 115° C. At this temperature, a solution of 9.8 g (0.06 mol) of triethoxysilane and 0.3 ml of an 0.02 molar $H_2PtCl_6.6H_2O$ catalyst solution in 25 ml of toluene are added dropwise in the course of 15 minutes, with stirring. The reaction mixture is then stirred for a further 15 hours, at 110° C. The solvent and excess triethoxysilane are removed in vacuo. After fractionation by Vigreux molecular path distillation, 15 g (=60% of theory) of dibutyl 3-[γ-(triethoxy)-silyl]-propoxy-phthalate are obtained as an oily product of boiling point 185° C./$10^{-2}$ mm Hg.

Analysis: Calculated: C 60.21% H 8.49% Si 5.63%; Found: C 60.7% H 8.3% Si 5.53%.

Di-n-butyl 3-allyloxy-phthalate, used as a starting material, can be prepared as follows: in a sulphonation flask, 150 ml of toluene are added to 61.8 g (0.3 mol) of 3-allyloxy-phthalic anhydride. 43 g (0.58 mol) of 1-butanol and 60.6 g (0.6 mol) of triethylamine are then added at 20°–25° C. (the reaction being slightly exothermic, with the temperature rising to 45° C.). The solution is stirred for 2 hours at 50° to 60° C. 81.8 g (0.6 mol) of 1-bromobutane are then added dropwise and the mixture is stirred for 2 hours at 50°–60° C. A further 30.3 g (0.3 mol) of triethylamine and 40.9 g (0.3 mol) of 1-bromobutane are then added. Stirring is then continued for 2 hours at 50°–60° C. and thereafter the triethylamine hydrobromide which has precipitated during the reaction is filtered off. The filtrate is concentrated in vacuo. The resulting yellow oil is then distilled in a bulb tube oven. 81 g (81% of theory) of di-n-butyl 3-allyloxy-phthalate are obtained as a fluorescent liquid (boiling point 152° C./0.075 mm Hg). $C_{19}H_{26}O_5$ (molecular weight 334.41).

Analysis: Calculated: C 68.24% H 7.84%; Found: C 68.3% H 7.7%.

EXAMPLE 11

In a sulphonation flask, 4.46 g (0.018 mol) of 4,4'-diaminodiphenylsulphone are dissolved in 80 ml of anhydrous DMA, under a nitrogen atmosphere, and 5.14 g (0.016 mol) of 3,3'-4,4'-benzophenone-tetracarboxylic acid dianhydride are added in portions at 0° C. The reaction mixture is stirred for one hour at 20°–25° C. A solution of 1.46 g (0.004 mol) of 3-propoxy-(methyl-di-n-propoxysilyl)-phthalic anhydride in 25 ml of DMA is then added at 0° C. and the reaction mixture is stirred for a further hour at 20°–25° C. The resulting polyamidoacid solution may be used as an adhesion promoter for finishing glass fibre fabrics which can be used for the production of glass fibre-reinforced laminates.

EXAMPLE 12

In a sulphonation flask, 1.98 g (0.01 mol) of 4,4'-diaminodiphenylmethane (DDM) are dissolved in 142 ml of anhydrous N,N'-dimethylformamide (DMF), under a nitrogen atmosphere, and 13.1 g (0.02 mol) of 4-N,N'-bis-[3-(tri-n-propoxy)-silyl-propyl]-aminophthalic anhydride are added dropwise at 0° C. The mixture is stirred for a further hour at 20°-25° C. The resulting amidoacid solution can be used for finishing glass fibres.

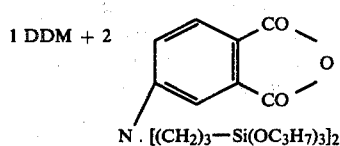

EXAMPLE 13

In a sulphonation flask, 4.32 g (0.04 mol) of 1,3-phenylenediamine are dissolved in 100 ml of anhydrous N,N'-dimethylacetamide, under a nitrogen atmosphere, and the solution is cooled to between −15° and −20° C. 7.17 g (0.03 mol) of sebacic acid dichloride are added dropwise to this solution, with stirring, under conditions such that the temperature does not rise above −15° C. The reaction mixture is then stirred for one hour at 20°-25° C. 3.04 g (0.03 mol) of triethylamine are then added dropwise at −15° C. After stirring for a further hour at 20° to 25° C., the reaction solution is cooled to 0° C. and a solution of 8.43 g (0.02 mol) of 4-[N-butyl-N'-(methyl-di-n-propoxy)-silyl-propyl]-aminophthalic anhydride (see Example 9) in 50 ml of N,N'-dimethylacetamide is added dropwise. The reaction solution is stirred for a further hour at 20°-25° C. After filtering off the triethylamine hydrochloride which has precipitated, the polyamidoacid solution obtained is used for finishing glass fibre fabrics.

USE EXAMPLES

Example I (use as adhesion promoter)

(a) Impregnation of a glass fibre fabric

A glass fibre fabric made from so-called E-glass, with Atlas binding and weighing 280 g/m$^2$, is first thermally desized to about 0.1% by weight residual size content and is then impregnated with 2% solutions of the adhesion promoters listed below. The adhesion promoter solutions are applied by immersion, with an impregnation speed of 0.5 m/minute, and the impregnated material is then dried for 20 minutes at 180° C. in a circulating air oven.

The prepregs obtained contain from 0.09 to 0.15% by weight, based on glass, of adhesion promoter.

The following are used as adhesion promoters (finishes):

(1) No adhesion promoter
(2) Vinyltris-(2-methoxyethoxy)-silane ("Silan A 172" from Messrs. Union Carbide), 2% solution in N,N-dimethylformamide (DMF)
(3) γ-Aminopropyl-triethoxysilane ("Silan A 1100" from Messrs. Union Carbide), 2% solution in N,N-dimethylformamide
(4) Chromium chloride methacrylate complex ("Volan-A" from Messrs. DuPont); 2% solution in DMF
(5) Polyamidoacid solution according to Preparation Example 5, diluted to 2% by weight with DMF
(6) Polyamide solution according to Preparation Example 6, diluted to 2% by weight with DMF
(7) Polyamide-amidoacid solution according to Preparation Example 7, diluted to 2% by weight with DMF
(8) Polyamidoacid solution according to Preparation Example 11, diluted to 2% by weight with DMF
(9) Polyamidoacid solution according to Preparation Example 12, diluted to 2% by weight with DMF
(10) Dibutyl 3-[γ-(triethoxy)-silyl]-propoxy-phthalate (Preparation Example 10), 2% solution in DMF
(11) 4-N,N'-bis-[3-(Tri-n-propoxy)-silyl-propyl]-aminophthalic anhydride (Preparation Example 8), 2% solution in DMF
(12) 3-N,N'-bis-[3-(Tri-n-propoxy)-silyl-propyl]-aminophthalic anhydride (Preparation Example 1), 2% solution in DMF.

(b) Production of copper-covered laminate sheets based on a bis-maleimide 1.0 mol of N,N'-4,4'-diphenylmethane-bis-maleimide is dissolved in 500 g of furfuryl alcohol at 100° C. and the solution is cooled to 25° C. 0.4 mol of 4,4'-diaminodiphenylmethane is dissolved in 200 g of methylglycol at 25° C. The two solutions are combined and mixed thoroughly. The glass fibre fabrics finished in accordance with section (a) are impregnated with this mixed solution by the immersion process at 25° C. and are then dried in a circulating air oven for 18 minutes at 180° C.; the resulting prepregs contain 39% by weight of resin.

10 layers of the impregnated fabric are then pressed hot between two 35 microns thick copper foils which have been pretreated by electrolytic surface coating with brass. The press is first kept under light contact pressure for 2 to 3 minutes; the pressure is then raised to 40 kp/cm$^2$ and the assembly is pressed for one hour at 180° C. The test specimens are then taken out of the press and post-cured for a further 6 hours in an oven at 240° C.; the resulting laminate sheets contain 35% by weight of resin.

(c) Production of copper-covered laminate sheets based on an epoxide resin (Triglycidyl ether based on dimethylhydantoin of the formula

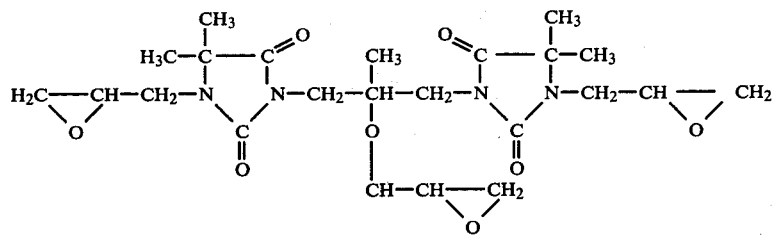

curing agent: cresyl novolac)

100 g of the above triglycidyl compound are dissolved in 25 g of acetone at 60° C. 66 g of the curing agent are dissolved in 30 g of acetone at 60° C. The two solutions are cooled to 25° C., combined with one another, with addition of 0.25 g of 2-phenylimidazole, and mixed thoroughly.

The glass fabrics finished in accordance with section (a) are impregnated by the immersion process at 25° C. and are then dried in a circulating air oven for 11 minutes at 150° C. The pressing procedure described under (b) is then carried out, followed by post-curing (10 hours at 200° C.).

(d) Production of copper-covered laminate sheets based on an epoxide resin

[Cycloaliphatic diepoxide (5 epoxy equivalents/kg) of the formula

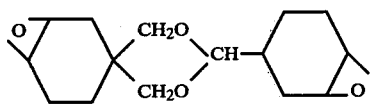

curing agent: boron trifluoride/amine complex]

125 g of the above diepoxide and 2 g of the curing agent are dissolved in acetone at 50° C. The solution is then cooled to 25° C. The finished glass fabrics are impregnated by the immersion process at 25° C. and are then dried in a circulating air oven for 6 minutes at 150° C. Thereafter the material is pressed for one hour at 160° C. analogously to section (b). After the pressing sequence, the laminates are post-cured for 3 hours in an oven at 180° C.

(e) Production of copper-covered laminate sheets based on an epoxide resin (80% solution of a diglycidyl ether of tetrabromobisphenol A in methyl ethyl ketone [2 epoxy equivalents/kg]; curing agent: 10% solution of dicyandiamide in methylglycol)

125 g of the above diglycidyl ether, 30 g of the curing agent, 0.2 g of benzyldimethylamine, 10 g of methylglycol and 10 g of acetone are combined, and mixed, at 25° C.

The glass fabrics finished in accordance with section (a) are impregnated by the immersion process at 25° C., and then in a circulating air oven for 10 minutes at 150° C., and pressed analogously to the procedure in section (b) for one hour at 180° C. (no post-curing).

Properties of the Copper-covered Laminate Sheets Obtained in Accordance with Example I (b), (c), (d) and (e).

Flexural strength in N/mm² according to ISO/R 178

(a) Initial value
(b) After 10 days' aging at 270° C.

Water absorption in % by weight, after 24 hours at 23° C. The measurements are carried out on flexural test specimens according to VSM Standard Specification 77,103.

Dielectric loss factor tg δ/50 c/s according to DIN 53,483

(a) Initial value measured at 23° C.
(b) After 6 hours' storage in boiling water Dielectric constant $\epsilon_r$/50 c/s according to DIN 53,483

(a) Initial value measured at 23° C.
(b) After 6 hours' storage in boiling water ISO/R = International Standards Organisation/Recommendations VSM = Verein Schweizerischer Maschinenindustrieller DIN = Deutsche Industrie-Norm The results are summarised in Tables I to IV which follow. The numbering of the experimental products and of the test specimens is the same as under (a).

Table I

| | (Test values of the laminate sheets according to Example 1b) |
|---|---|
| | Adhesion promoter Product No. |

| | 1 | 2 | 3 | 4 | 5 | 6 | 7 | 8 | 9 | 10 |
|---|---|---|---|---|---|---|---|---|---|---|
| Flexural strength, N/mm², initial value | 422.3 | 401 | 586.7 | 553.2 | 569.4 | 603.6 | 455.4 | 436.4 | 349.1 | 443.2 |
| After 10 days' aging at 270° C. | 282.4 | 108.8 | 162.8 | 220.3 | 296.1 | 458.2 | 325.5 | 318.4 | 207.2 | 277.6 |
| Water absorption in % by weight after 24 hours at 23° C. | 0.54 | 0.28 | 0.29 | 0.23 | 0.13 | 0.08 | 0.18 | 0.25 | 0.22 | — |
| Dielectric loss factor, δ/50 c/s, initial value | 1.08 | 1.15 | 2.71 | 0.86 | 0.31 | 0.29 | 0.28 | 0.26 | 0.27 | 0.25 |
| After 6 hours' storage in boiling water | 6.57 | 2.81 | 4.22 | 1.93 | 1.40 | 0.96 | 0.49 | 0.39 | 0.40 | 1.00 |
| Dielectric constant $\epsilon_r$/50 c/s, initial | | | | | | | | | | |

Table I-continued (Test values of the laminate sheets according to Example 1b)

| | Adhesion promoter Product No. | | | | | | | | | |
|---|---|---|---|---|---|---|---|---|---|---|
| | 1 | 2 | 3 | 4 | 5 | 6 | 7 | 8 | 9 | 10 |
| value | 5.1 | 5.4 | 5.1 | 6.6 | 5.2 | 5.2 | 5.0 | 5.1 | 5.0 | 5.3 |
| After 6 hours' storage in boiling water | 6.9 | 5.8 | 5.5 | 7.9 | 5.7 | 5.5 | 5.2 | 5.4 | 5.2 | 5.5 |

Table II (Test values of the laminate sheets according to Example Ic)

| | Adhesion promoter - Product No. | | | | |
|---|---|---|---|---|---|
| | 1 | 4 | 9 | 11 | 12 |
| Flexural strength, N/mm$^2$, initial value | 342.5 | 523.4 | 318.8 | 302.6 | 303.8 |
| After 10 days' aging at 220° C. | 358.0 | 469.1 | 314.8 | 310.1 | 320.6 |
| After 6 hours' storage in boiling water | 328.5 | 440.7 | 365.3 | 361.7 | 408.5 |
| Change in % | −4.1 | −15.8 | +14.6 | +19.5 | +34.5 |
| Dielectric loss factor, δ/50 c/s, initial value | 0.40 | 0.46 | 0.45 | 0.38 | 0.44 |
| After 6 hours' storage in boiling water | 3.44 | 2.01 | 1.14 | 0.98 | 1.01 |
| Dielectric constant $\epsilon_r$/50 c/s, initial value | 5.3 | 4.9 | 4.8 | 4.5 | 4.8 |
| After 6 hours' storage in boiling water | 6.4 | 5.8 | 5.1 | 4.9 | 5.1 |

Table III (Test values of the laminate sheets according to Example Id)

| | Adhesion promoter - Product No. | | | | |
|---|---|---|---|---|---|
| | 1 | 4 | 8 | 9 | 12 |
| Flexural strength, N/mm$^2$, initial value | 329.5 | 421.4 | 361.5 | 328.3 | 289.9 |
| After 20 days' aging at 220° C. | 295.3 | 397.7 | 349.6 | 299.7 | 222.7 |
| After 6 hours' storage in boiling water | | | | | |
| Change in % | | | | | |
| Dielectric loss factor, δ/50 c/s, initial value | 0.35 | 0.37 | 0.30 | 0.30 | 0.34 |
| After 6 hours' storage in boiling water | 1.64 | 1.64 | 1.27 | 1.25 | 1.09 |
| Dielectric constant $\epsilon_r$/50 c/s, initial value | 4.3 | 4.2 | 4.0 | 4.1 | 4.0 |
| After 6 hours' storage in boiling water | 4.5 | 4.5 | 4.3 | 4.4 | 4.3 |

Table IV (Test values of the laminate sheets according to Example Ie)

| | Adhesion promoter - Product No. | | | | |
|---|---|---|---|---|---|
| | 1 | 4 | 9 | 11 | 12 |
| Flexural strength, N/mm$^2$, initial value | 373.5 | 530.9 | 354.3 | 340.0 | 360.0 |
| After 6 days' aging at 180° C. | 321.4 | 519.8 | 329.7 | 333.6 | 310.1 |
| After 6 hours' storage in boiling water | 222.8 | 475.4 | 375.7 | 376.2 | 388.8 |
| Change in % | −40.4 | −10.5 | +6.0 | +10.6 | +8.0 |
| Dielectric loss factor, δ/50 c/s, initial value | 0.38 | 0.45 | 0.34 | 0.27 | 0.30 |
| After 6 hours' storage in boiling water | 39.10 | 4.05 | 3.62 | 2.69 | 2.68 |
| Dielectric constant $\epsilon_r$/50 c/s, initial value | 5.0 | 5.0 | 4.9 | 4.9 | 5.0 |
| After 6 hours' storage in boiling water | | | | | |
| age in boiling water | 16.3 | 5.7 | 5.5 | 5.5 | 5.5 |

EXAMPLE II (use as a curing agent for epoxide resins)

14.41 g of epoxide resin A (epoxide content 5.20 epoxide equivalents/kg), 9.0 g of phthalic anhydride and 4.43 g of the 3-N,N-bis-[3-tri-n-propoxy)-silyl-propyl-]aminophthalic anhydride prepared according to Example 1 (the total weight of the two anhydrides corresponds to 0.9 mol per equivalent of epoxide groups) are mixed and the mixture is warmed to 125° C. in the course of one hour, whilst stirring. After adding a few drops of benzyldimethylamine, the reaction sollution is rapidly poured into an aluminum mould, pre-warmed to 120° C., in order to produce 4 mm thick sheets. Curing takes place in a circulating air oven, first for 4 hours at 120° C. and then for 16 hours at 160° C. Bubble-free castings are obtained, having a flexural strength of 127 N/mm$^2$, a deflection of 6 mm and a modulus of elasticity of 2,760 N/mm$^2$. The water absorption at 23° C. is 0.21% by weight after 4 days and 0.37% by weight after 10 days.

EXAMPLE III (use as a curing agent for epoxide resins)

Analogously to the procedure described in Example II, 14.41 g of epoxide resin A (epoxide content 5.20 epoxide equivalents/kg), 8.0 g (0.054 mol) of phthalic anhydride and 8.85 g (0.0135 mol) of the 3-N,N-bis-[3-(tri-n-propoxy)-silyl-propyl]-aminophthalic anhydride prepared according to Example 1 (the total weight of the two anhydrides corresponds to 0.9 mol per equivalent of epoxide groups) are mixed and converted to bubble-free castings. The flexural strength is 106 N/mm$^2$, the deflection is 8 mm, the modulus of elasticity is 2,540 N/mm$^2$ and the water absorption at 23° C. is 0.28% by weight after 4 days and 0.39% by weight after 10 days.

Example IV (use as a curing agent for epoxide resins)

Analogously to the procedure described in Example II, 9.6 g of epoxide resin A (epoxide content 5.20 epoxide equivalents/kg), 4.66 g (0.0315 mol) of phthalic anhydride and 5.9 g (0.0135 mol) of the 3-N-ethyl-N-(tri-n-propoxy)silyl-propyl-aminophthalic anhydride prepared according to Example 3 (the total weight of the two anhydrides corresponds to 0.9 mol per equivalent of epoxide groups) are mixed and converted to transparent, bubble-free castings.

Example V (use as a curing agent for epoxide resins)

Analogously to the procedure described in Example II, 9.6 g of epoxide resin A (epoxide content 5.20 epoxide equivalents/kg), 5.33 g (0.036 mol) of phthalic anhydride and 3.3 g (0.009 mol) of the 3-(γ-tri-n-propoxysilyl)propoxy-phthalic anhydride prepared according to Example 4 are mixed and converted to transparent, bubble-free castings.

What we claim is:

1. A compound of the formula I

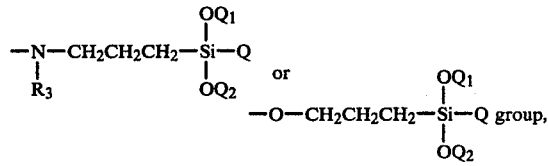

(I)

in which $R_1$ and $R_2$ independently of one another are —OH, alkoxy with 1-12 C atoms or phenoxy or $R_1$ and $R_2$ together are the —O— group, X is a

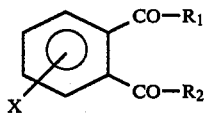

$R_3$ is alkyl with 2-7 C atoms, cycloalkyl with 5-7 C atoms, benzyl or

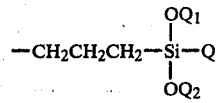

Q is methyl, phenyl or —OQ$_3$ and Q$_1$, Q$_2$ and Q$_3$ independently of one another are alkyl with 1-6 C atoms or phenyl.

2. A compound of the formula I according to claim 1, in which $R_1$ and $R_2$ together are —O—.

3. A compound of the formula I according to claim 1, in which the grouping X is bonded to the benzene ring in the 3-position.

4. A compound of the formula I according to claim 1, in which $R_1$ and $R_2$ together are the —O— group, X is a

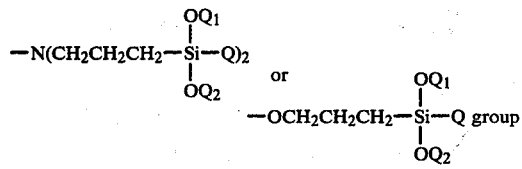

bonded in the 3-position, Q is methyl or alkoxy with 1-4 C atoms and Q$_1$ and Q$_2$ are each alkyl with 1-4 C atoms.

* * * * *